United States Patent
Huang

(10) Patent No.: US 10,993,893 B2
(45) Date of Patent: May 4, 2021

(54) LIQUID EYELINER AND MANUFACTURING METHOD THEREOF

(71) Applicant: HANGZHOU OCEAN PEARL INDUSTRIAL CO., LTD, Hangzhou (CN)

(72) Inventor: Juanxiu Huang, Hangzhou (CN)

(73) Assignee: HANGZHOU OCEAN PEARL INDUSTRIAL CO., LTD, Hangzhou (CN)

(*) Notice: Subject to any disclaimer, the term of this patent is extended or adjusted under 35 U.S.C. 154(b) by 0 days.

(21) Appl. No.: 16/536,341

(22) Filed: Aug. 9, 2019

(65) Prior Publication Data

US 2021/0015723 A1  Jan. 21, 2021

(30) Foreign Application Priority Data

Jul. 19, 2019  (CN) .......................... 201910652834.3

(51) Int. Cl.

| A61K 8/19 | (2006.01) |
|---|---|
| A61K 8/34 | (2006.01) |
| A61K 8/81 | (2006.01) |
| A61K 8/89 | (2006.01) |
| A61K 8/9789 | (2017.01) |
| A61K 8/9794 | (2017.01) |
| A61Q 1/10 | (2006.01) |

(52) U.S. Cl.
CPC ................ *A61K 8/19* (2013.01); *A61K 8/345* (2013.01); *A61K 8/8158* (2013.01); *A61K 8/8182* (2013.01); *A61K 8/89* (2013.01); *A61K 8/9789* (2017.08); *A61K 8/9794* (2017.08); *A61Q 1/10* (2013.01)

(58) Field of Classification Search
None
See application file for complete search history.

(56) References Cited

FOREIGN PATENT DOCUMENTS

CN  109674689 A  *  4/2019

OTHER PUBLICATIONS

Derwent Summary for CN109674689A (Year: 2019).*
Hilmas, "Riot Control Agents", Handbook of Toxicology Chemical Warfare Agents, 2nd edition, Chapter 11, pp. 131-150 (Year: 2015).*

* cited by examiner

*Primary Examiner* — Bethany P Barham
*Assistant Examiner* — Barbara S Frazier

(57) ABSTRACT

The present disclosure provides a liquid eyeliner and a manufacturing method thereof. The liquid eyeliner includes following components by weight: acrylic acid octyl acrylamide copolymer or propylene ester octyl acrylamide copolymer ranging from 4-9%, propylene glycol provided ranging from 5-7%, ethylhexylglycerin ranging from 0.1-0.6%, butanediol ranging from 1.5-4%, sorbitan oleate ranging from 1-2%, emulsifier ranging from 1.4-2.2%, polydimethylsiloxane ranging from 6-9%, polyvinylpyrrolidone ranging from 3-4%, sorbitan sesquioleate ranging from 1.2-2%, butylated hydroxytoluene ranging from 0.1-0.2%, methylparaben ranging from 0.1-0.3%, propylparaben ranging from 0.05-0.15%, phenoxyethanol ranging from 0.6-1.2%, essence ranging from 0.1-0.3%, carbon black ranging from 1.5-2.8%, iron oxide black ranging from 30-45%, deionized water ranging from 22-30%, and plant extract ranging from 0.1-0.3%.

3 Claims, No Drawings

LIQUID EYELINER AND MANUFACTURING METHOD THEREOF

TECHNICAL FIELD

The present disclosure relates to a field of cosmetic technology, and in particular to a multifunctional liquid eyeliner.

BACKGROUND

Everyone is pursuing beauty. Women in Asia like to use an eyeliner to outline a more pleasing eye makeup, showing three-dimensionality of the eyes, making the eyes look deeper. As a make-up product, the eyeliner has become a "people's product."

Compared with a conventional eyeliner, a liquid eyeliner has advantages such as precise fit, smoothness, and softness. Because the liquid eyeliner is liquid, it can draw the eyes with beautiful luster and with a three-dimensional effect. However, the eyeliner is prone to uneven liquid volume or discharges either too much or too little when applied, whereas the liquid eyeliner is more maneuverable and more and more popular with consumers.

The conventional eyeliner mostly consists of organic components, and its role is only to personalize modification and beauty, and there is no additional function. With enrichment of beauty products and upgrading of technology, there is a need for an eyeliner product that not only takes beauty of the eyes into account, but also comes with special functions, such as auxiliary fixing false eyelashes.

SUMMARY

The present disclosure provides a liquid eyeliner to solve a technical problem set forth above.

To achieve the above object, the present disclosure provides a liquid eyeliner. The liquid eyeliner includes following components by weight:
acrylic acid octyl acrylamide copolymer or propylene ester octyl acrylamide copolymer provided in an amount ranging from 4-9%,
propylene glycol provided in an amount ranging from 5-7%,
ethylhexylglycerin provided in an amount ranging from 0.1-0.6%,
butanediol provided in an amount ranging from 1.5-4%,
sorbitan oleate provided in an amount ranging from 1-2%,
emulsifier provided in an amount ranging from 1.4-2.2%
polydimethylsiloxane provided in an amount ranging from 6-9%,
polyvinylpyrrolidone provided in an amount ranging from 3-4% by weight relative to the total weight of the liquid eyeliner,
sorbitan sesquioleate provided in an amount ranging from 1.2-2%,
butylated hydroxytoluene provided in an amount ranging from 0.1-0.2% by weight relative to the total weight of the liquid eyeliner,
methylparaben provided in an amount ranging from 0.1-0.3%,
propylparaben provided in an amount ranging from 0.05-0.15%,
phenoxyethanol provided in an amount ranging from 0.6-1.2%,
essence provided in an amount ranging from 0.1-0.3%,
carbon black provided in an amount ranging from 1.5-2.8%,
iron oxide black provided in an amount ranging from 30-45%,
deionized water provided in an amount ranging from 22-30%, and
plant extract provided in an amount ranging from 0.1-0.3%.

Furthermore, specific components of the liquid eyeliner are as follows:
acrylic acid octyl acrylamide copolymer or propylene ester octyl acrylamide copolymer provided in an amount ranging from 4-9%,
propylene glycol provided in an amount ranging from 5-7%,
ethylhexylglycerin provided in an amount ranging from 0.1-0.6%,
butanediol provided in an amount ranging from 1.5-4%,
sorbitan oleate provided in an amount ranging from 1-2%,
emulsifier provided in an amount ranging from 1.4-2.2%,
polydimethylsiloxane provided in an amount ranging from 6-9%,
polyvinylpyrrolidone provided in an amount ranging from 3-4%,
sorbitan sesquioleate provided in an amount ranging from 1.2-2%,
butylated hydroxytoluene provided in an amount ranging from 0.1-0.2%,
methylparaben provided in an amount ranging from 0.1-0.3%,
propylparaben provided in an amount ranging from 0.05-0.15%,
phenoxyethanol provided in an amount ranging from 0.6-1.2%,
essence provided in an amount ranging from 0.1-0.3%,
carbon black provided in an amount ranging from 1.5-2.8%,
iron oxide black provided in an amount ranging from 30-45%,
deionized water provided in an amount ranging from 22-30%, and
plant extract provided in an amount ranging from 0.1-0.3%.

Furthermore, essence is selected from at least one of rose ether, rose alcohol, hydroxycitronellal, amyl salicylate, linalool, and linalyl acetate.

Furthermore, the plant extract is selected from at least three three of mulberry extract, angelica extract, ginger root extract, chrysanthemum extract, and alfalfa extract.

The present disclosure further provides a manufacturing method of a liquid eyeliner. The method includes steps:
S1: weighing components separately by weight relative to a total weight of the liquid eyeliner:
providing acrylic acid octyl acrylamide copolymer or propylene ester octyl acrylamide copolymer in an amount of 7.8%;
providing propylene glycol in an amount of 5.2%;
providing ethylhexylglycerin in an amount of 0.5%;
providing butanediol in an amount of 3.6%;
providing sorbitan oleate in an amount of 1.2%;
providing emulsifier in an amount of 1.8%;
providing polydimethylsiloxane in an amount of 8.6%;
providing polyvinylpyrrolidone in an amount of 3.1%;
providing sorbitan sesquioleate in an amount of 1.6%;
providing butylated hydroxytoluene in an amount of 0.1%;
providing methylparaben in an amount of 0.2%;
providing propylparaben in an amount of 0.1%;
providing phenoxyethanol in an amount of 0.8%;
providing essence in an amount of 0.1%;
providing carbon black in an amount of 1.6%;
providing iron oxide black in an amount of 37%;
providing deionized water in an amount of 26.5%; and
providing plant extract in an amount of 0.2%;

S2: mixing, heating, and stirring the acrylic acid octyl acrylamide copolymer/propylene ester octyl acrylamide copolymer, the propylene glycol, the ethylhexylglycerin, the butanediol, the sorbitan oleate, the emulsifier, the polydimethylsiloxane, the polyvinylpyrrolidone, the sorbitan sesquioleate, the butylated hydroxytoluene, and the phenoxyethanol with the deionized water until they are completely dissolved to obtain a mixed solution; and S3: adding the methylparaben, the propylparaben, the essence, the carbon black, the iron oxide black, and the plant extract into the mixed solution, and stirring them until they are completely dissolved to obtain the liquid eyeliner.

The liquid eyeliner of the present disclosure includes magnetic materials and the plant extract. The magnetic materials have strong magnetic property, and are able to adsorb magnetic false eyelashes, which makes a wearing of the magnetic false eyelashes simpler and more efficient. The plant extract is able to effectively promote a micro-circulation of blood capillary, and improves small winkles of the eyes. Further, the plant extract provides nutrients to eye skin, promote a metabolism of the eye skin, and achieve comprehensive conditioning and soothe eye fatigue.

DETAILED DESCRIPTION

Technical solutions in the embodiments of the present disclosure are clearly and completely described below. It is obvious that the described embodiments are only a part of the present disclosure, and not referring to all of the embodiments. All other embodiments obtained by those skilled in the art based on the embodiments of the present disclosure without creative efforts are within the scope of the present disclosure.

Embodiment 1

The present disclosure provides a liquid eyeliner. The liquid eyeliner includes the following compounds by weight:
acrylic acid octyl acrylamide copolymer or propylene ester octyl acrylamide copolymer
provided in an amount ranging from 4-9%,
propylene glycol provided in an amount ranging from 5-7%,
ethylhexylglycerin provided in an amount ranging from 0.1-0.6%,
butanediol provided in an amount ranging from 1.5-4%,
sorbitan oleate provided in an amount ranging from 1-2%,
emulsifier provided in an amount ranging from 1.4-2.2,
polydimethylsiloxane provided in an amount ranging from 6-9%,
polyvinylpyrrolidone provided in an amount ranging from 3-4%,
sorbitan sesquioleate provided in an amount ranging from 1.2-2%,
butylated hydroxytoluene provided in an amount ranging from 0.1-0.2%,
methylparaben provided in an amount ranging from 0.1-0.3%,
propylparaben provided in an amount ranging from 0.05-0.15%,
phenoxyethanol provided in an amount ranging from 0.6-1.2%,
essence provided in an amount ranging from 0.1-0.3%,
carbon black provided in an amount ranging from 1.5-2.8%,
iron oxide black provided in an amount ranging from 30-45%,
deionized water provided in an amount ranging from 22-30%, and
plant extract provided in an amount ranging from 0.1-0.3%.

To be specific, specific components of the liquid eyeliner are as follows:
the acrylic acid octyl acrylamide copolymer or the propylene ester octyl acrylamide copolymer is provided in an amount of 7.8% by weight,
the propylene glycol is provided in an amount of 5.2%,
the ethylhexylglycerin is provided in an amount of 0.5%,
the butanediol is provided in an amount of 3.6%,
the sorbitan oleate is provided in an amount of 1.2%,
the emulsifier is provided in an amount of 1.8%,
the polydimethylsiloxane is provided in an amount of 8.6%,
the polyvinylpyrrolidone is provided in an amount of 3.1%,
the sorbitan sesquioleate is provided in an amount of 1.6%,
the butylated hydroxytoluene is provided in an amount of 0.1%,
the methylparaben is provided in an amount of 0.2%,
the propylparaben is provided in an amount of 0.1%,
the phenoxyethanol is provided in an amount of 0.8%,
the essence is provided in an amount of 0.1%,
the carbon black is provided in an amount of 1.6%,
the iron oxide black is provided in an amount of 37%;
the deionized water is provided in an amount of 26.5%, and
the plant extract is provided in an amount of 0.2%.

To be specific, the emulsifier is stearyl-21.

The present disclosure further provides a manufacturing method of the liquid eyeliner. The method includes steps:
S1: weighing components separately by weight relative to a total weight of the liquid eyeliner:
providing acrylic acid octyl acrylamide copolymer or propylene ester octyl acrylamide copolymer in an amount of 7.8% by weight;
providing propylene glycol in an amount of 5.2%;
providing ethylhexylglycerin in an amount of 0.5%;
providing butanediol in an amount of 3.6%;
providing sorbitan oleate in an amount of 1.2%;
providing emulsifier in an amount of 1.8%;
providing polydimethylsiloxane in an amount of 8.6%;
providing polyvinylpyrrolidone in an amount of 3.1%;
providing sorbitan sesquioleate in an amount of 1.6%;
providing butylated hydroxytoluene in an amount of 0.1%;
providing methyl paraben in an amount of 0.2%;
providing propylparaben in an amount of 0.1%;
providing phenoxyethanol in an amount of 0.8%;
providing essence in an amount of 0.1%;
providing carbon black in an amount of 1.6%;
providing iron oxide black in an amount of 37%;
providing deionized water in an amount of 26.5%; and
providing plant extract in an amount of 0.2%;
S2: mixing, heating, and stirring the acrylic acid octyl acrylamide copolymer or propylene ester octyl acrylamide copolymer, the propylene glycol, the ethylhexylglycerin, the butanediol, the sorbitan oleate, the emulsifier, the polydimethylsiloxane, the polyvinylpyrrolidone, the sorbitan sesquioleate, the butylated hydroxytoluene, and the phenoxyethanol with the deionized water until they are completely dissolved to obtain a mixed solution; and
S3: adding the methylparaben, the propylparaben, the essence, the carbon black, the iron oxide black, and the plant extract into the mixed solution, and stirring them until they are completely dissolved to obtain the liquid eyeliner.

Embodiment 2

The present disclosure further provides a manufacturing method of the liquid eyeliner. The method includes steps:

S1: weighing components separately by weight relative to a total weight of the liquid eyeliner:
providing acrylic acid octyl acrylamide copolymer or propylene ester octyl acrylamide copolymer in an amount of 7.2% by weight;
providing propylene glycol in an amount of 5.2%;
providing ethylhexylglycerin in an amount of 0.3%;
providing butanediol in an amount of 3.6%;
providing sorbitan oleate in an amount of 1.5%;
providing emulsifier in an amount of 1.8%;
providing polydimethylsiloxane in an amount of 8.6%;
providing polyvinylpyrrolidone in an amount of 3.1%;
providing sorbitan sesquioleate in an amount of 1.6%;
providing butylated hydroxytoluene in an amount of 0.1%;
providing methylparaben in an amount of 0.2%;
providing propylparaben in an amount of 0.1%;
providing phenoxyethanol in an amount of 0.8%;
providing essence in an amount of 0.2%;
providing carbon black in an amount of 1.8%;
providing iron oxide black in an amount of 37.3%;
providing deionized water in an amount of 26.5%; and
providing plant extract in an amount of 0.1%;
S2 mixing, heating, and stirring the acrylic acid octyl acrylamide copolymer or propylene ester octyl acrylamide copolymer, the propylene glycol, the ethylhexylglycerin, the butanediol, the sorbitan oleate, the emulsifier, the polydimethylsiloxane, the polyvinylpyrrolidone, the sorbitan sesquioleate, the butylated hydroxytoluene, and the phenoxyethanol with the deionized water until they are completely dissolved to obtain a mixed solution; and
S3: adding the methylparaben, the propylparaben, the essence, the carbon black, the iron oxide black, and the plant extract into the mixed solution, and stirring them until they are completely dissolved to obtain the liquid eyeliner.

Materials and manufacturing steps of embodiment 2 is same as the above-mentioned embodiment 1, except for a ratio of the components.

Embodiment 3

The present disclosure further provides a manufacturing method of the liquid eyeliner. The method includes steps:
S1: weighing components separately by weight relative to a total weight of the liquid eyeliner:
providing acrylic acid octyl acrylamide copolymer or propylene ester octyl acrylamide copolymer in an amount of 7.5% by weight;
providing propylene glycol in an amount of 5.1%;
providing ethylhexylglycerin in an amount of 0.5%;
providing butanediol in an amount of 3.2%;
providing sorbitan oleate in an amount of 1.2%;
providing emulsifier in an amount of 1.8%;
providing polydimethylsiloxane in an amount of 8.8%;
providing polyvinylpyrrolidone in an amount of 3.1%;
providing sorbitan sesquioleate in an amount of 1.8%;
providing butylated hydroxytoluene in an amount of 0.1%;
providing methylparaben in an amount of 0.2%;
providing propylparaben in an amount of 0.1%;
providing phenoxyethanol in an amount of 0.6%;
providing essence in an amount of 0.2%;
providing carbon black in an amount of 1.8%;
providing iron oxide black in an amount of 36.5%,
providing deionized water in an amount of 27.4%; and
providing plant extract in an amount of 0.1%;
S2: mixing, heating, and stirring the acrylic acid octyl acrylamide copolymer or propylene ester octyl acrylamide copolymer, the propylene glycol, the ethylhexylglycerin, the butanediol, the sorbitan oleate, the emulsifier, the polydimethylsiloxane, the polyvinylpyrrolidone, the sorbitan sesquioleate, the butylated hydroxytoluene, and the phenoxyethanol with the deionized water until they are completely dissolved to obtain a mixed solution; and
S3: adding the methylparaben, the propylparaben, the essence, the carbon black, the iron oxide black, and the plant extract into the mixed solution, and stirring thein until they are completely dissolved to obtain the liquid eyeliner.

Materials and manufacturing steps of embodiment 3 is same as the above-mentioned two embodiments, except for the ratio of the components.

The multifunctional liquid eyeliner manufactured according to the ratio of the components and the manufacturing method described in embodiment 1-3 has been tested for its adsorption and fatigue resistance to magnetic eyelashes, and the results were passed through A, B, C, and D, where A stands for the best, and D stands for the worst. The assessment is as follows:

| Embodiment | Adsorption to magnetic false eyelashes | Fatigue resistance |
| --- | --- | --- |
| Embodiment 1 | A | A |
| Embodiment 2 | B | A |
| Embodiment 3 | A | B |

The liquid eyeliner of the present disclosure includes magnetic materials and the plant extract. The magnetic materials have a strong magnetic property, and are able to adsorb magnetic false eyelashes, which makes wearing of the magnetic false eyelashes simpler and more efficient. The plant extract is able to effectively promote micro-circulation of blood capillary, and improves small winkles of the eyes. Further, the plant extract provides nutrients to eye skin, promote metabolism of the eye skin, and achieve comprehensive conditioning and soothe eye fatigue.

The above content is a further detailed description of the present disclosure in conjunction with the specific preferred embodiments, and the specific implementation of the present disclosure is not limited to the description. It will be apparent to those skilled in the art that a number of simple deductions or substitutions may be made without departing from the principle and conception of the present disclosure, which should be considered as being within the scope of the present disclosure

What is claimed is:
1. A liquid eyeliner, comprising following compounds by weight:
acrylic acid octyl acrylamide copolymer or propylene ester octyl acrylamide copolymer provided in an amount ranging from 4-9%,
propylene glycol provided in an amount ranging from 5-7%,
ethylhexylglycerin provided in an amount ranging from 0.1-0.6%,
butanediol provided in an amount ranging from 1.5-4%,
sorbitan oleate provided in an amount ranging from 1-2%,
emulsifier provided in an amount ranging from 1.4-2.2%,
polydimethylsiloxane provided in an amount ranging from 6-9%,
polyvinylpyrrolidone provided in an amount ranging from 3-4%, sorbitan sesquioleate provided in an amount ranging from 1.2-2%,
butylated hydroxytoluene provided in an amount ranging from 0.1-0.2%,
methylparaben provided in an amount ranging from 0.1-0.3%,
propylparaben provided in an amount ranging from 0.05-0.15%,
phenoxyethanol provided in an amount ranging from 0.6-1.2%,
essence provided in an amount ranging from 0.1-0.3%,
carbon black provided in an amount ranging from 1.5-2.8%,
iron oxide black provided in an amount ranging from 30-45%,
deionized water provided in an amount ranging from 22-30%, and
plant extract provided in an amount ranging from 0.1-0.3%,
wherein the essence is selected from at least one of rose ether, rose alcohol, hydroxycitronellal, amyl salicylate, linalool, and linalyl acetate,
and wherein the plant extract is selected from at least three of mulberry extract, angelica extract, ginger root extract, chrysanthemum extract, and alfalfa extract.

2. The liquid eyeliner according to claim 1, wherein the emulsifier is stearyl-21.

3. A manufacturing method of a liquid eyeliner according to claim 1, comprising steps:
S1: weighing components separately by weight relative to a total weight of the liquid eyeliner:
providing acrylic acid octyl acrylamide copolymer or propylene ester octyl acrylamide copolymer provided in an amount ranging from 4-9%,
providing propylene glycol provided in an amount ranging from 5-7%,
providing ethylhexylglycerin provided in an amount ranging from 0.1-0.6%,
providing butanediol provided in an amount ranging from 1.5-4%,
providing sorbitan oleate provided in an amount ranging from 1-2%,
providing emulsifier provided in an amount ranging from 1.4-2.2%,
providing polydimethylsiloxane provided in an amount ranging from 6-9%,
providing polyvinylpyrrolidone provided in an amount ranging from 3-4%,
providing sorbitan sesquioleate provided in an amount ranging from 1.2-2%,
providing butylated hydroxytoluene provided in an amount ranging from 0.1-0.2%,
providing methylparaben provided in an amount ranging from 0.1-0.3%,
providing propylparaben provided in an amount ranging from 0.05-0.15%,
providing phenoxyethanol provided in an amount ranging from 0.6-1.2%,
providing essence provided in an amount ranging from 0.1-0.3%,
providing carbon black provided in an amount ranging from 1.5-2.8%,
providing iron oxide black provided in an amount ranging from 30-45%,
providing deionized water provided in an amount ranging from 22-30%, and
providing plant extract provided in an amount ranging from 0.1-0.3%,
S2: mixing, heating, and stirring the acrylic acid octyl acrylamide copolymer/propylene ester octyl acrylamide copolymer, the propylene glycol, the ethylhexylglycerin, the butanediol, the sorbitan oleate, the emulsifier, the polydimethylsiloxane, the polyvinylpyrrolidone, the sorbitan sesquioleate, the butylated hydroxytoluene, and the phenoxyethanol with the deionized water until they are completely dissolved to obtain a mixed solution; and
S3: adding the methylparaben, the propylparaben, the essence, the carbon black, the iron oxide black, and the plant extract into the mixed solution, and stirring them until they are completely dissolved to obtain the liquid eyeliner wherein the essence is selected from at least one of rose ether, rose alcohol, hydroxycitronellal, amyl salicylate, linalool, and linalyl acetate,
and wherein the plant extract is selected from at least three of mulberry extract, angelica extract, ginger root extract, chrysanthemum extract, and alfalfa extract.

\* \* \* \* \*